United States Patent
Lachner et al.

(10) Patent No.: US 10,056,158 B2
(45) Date of Patent: *Aug. 21, 2018

(54) DETERMINATION OF ENHANCING STRUCTURES IN AN ANATOMICAL BODY PART

(71) Applicant: Brainlab AG, Munich (DE)

(72) Inventors: Rainer Lachner, Munich (DE);
Rowena Thomson, Kirchheim (DE);
Christina von Freyberg, Tirschenreuth (DE)

(73) Assignee: Brainlab AG, Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/819,995

(22) Filed: Nov. 21, 2017

(65) Prior Publication Data

US 2018/0158547 A1 Jun. 7, 2018

Related U.S. Application Data

(63) Continuation of application No. 15/034,485, filed as application No. PCT/EP2013/073053 on Nov. 5, 2013, now Pat. No. 9,858,674.

(51) Int. Cl.
*G06T 7/187* (2017.01)
*G06T 7/11* (2017.01)
(Continued)

(52) U.S. Cl.
CPC .............. *G16H 30/40* (2018.01); *G06T 5/002* (2013.01); *G06T 5/20* (2013.01); *G06T 7/001* (2013.01); *G06T 7/0012* (2013.01); *G06T 7/11* (2017.01); *G06T 7/136* (2017.01); *G06T 7/174* (2017.01); *G06T 7/187* (2017.01); *G06T 7/60* (2013.01); *G06T 2207/10096* (2013.01); *G06T 2207/20128* (2013.01); *G06T 2207/20156* (2013.01); *G06T 2207/20224* (2013.01); *G06T 2207/30016* (2013.01); *G06T 2207/30096* (2013.01)

(58) Field of Classification Search
CPC . G06T 2207/10096; G06T 2207/20128; G06T 2207/20156; G06T 2207/20224; G06T 2207/30016; G06T 2207/30096; G06T 5/002; G06T 5/20; G06T 7/001; G06T 7/0012; G06T 7/0081; G06T 7/60; G06T 2207/20141; G06T 2207/20148; G06T 7/0097; G06T 7/11; G06T 7/136; G06T 7/174; G06T 7/187
See application file for complete search history.

(56) References Cited

U.S. PATENT DOCUMENTS 8,280,133 B2 10/2012 Wels et al.
2009/0052763 A1 2/2009 Mausumi et al.

FOREIGN PATENT DOCUMENTS

EP 1441310 A2 7/2004

OTHER PUBLICATIONS

European Patent Office, Communication issued in EP Application No. 13788953.1 dated Oct. 30, 2017.
(Continued)

*Primary Examiner* — Siamak Harandi
(74) *Attorney, Agent, or Firm* — Middleton Reutlinger

(57) ABSTRACT

A data processing method for determining an enhancing structure of interest within an anatomical body part, wherein the structure of interest exhibits an enhanced signal in an image of the anatomical body part generated by a medical imaging method using a contrast agent, said method being designed to be performed by a computer and comprising a region growing algorithm.

15 Claims, 6 Drawing Sheets

(51) Int. Cl.
    *G16H 30/40*    (2018.01)
    *G06T 7/136*    (2017.01)
    *G06T 5/00*     (2006.01)
    *G06T 5/20*     (2006.01)
    *G06T 7/00*     (2017.01)
    *G06T 7/60*     (2017.01)
    *G06T 7/174*    (2017.01)

(56) References Cited

OTHER PUBLICATIONS

Kanaly, Charles W. et al. "A Novel Method of Volumetric MRI Response Assessment of Enhancing Brain Tumors" Plos One, vol. 6, No. 1, Jan. 26, 2011.
Adams, R. et al. "Seeded Region Growing" Patter Analysis and Machine Intelligence, vol. 16, No. 6, Jun. 1, 1994.
Niikravanshalmani, Alireza et al. "Three-Dimensional Semi-Automatic Segmentation of Intracranial Aneurysms in CTA" Information Tehcnology and Applications in Biomedicine, Nov. 3, 2010.
Vincent, L. "Morphological Grayscale Reconstruction in Image Analysis: Applications and Efficient Algorithms" IEEE Transactions on Image Processing, vol. 2, No. 2, Apr. 1, 1993.
Schnack, H.G. et al. "Automatic Segmentation of the Ventricular System from MRI Images of the Human Brain" Neuroimage, vol. 31, No. 8, May 1, 2001.
Gordillo, Nelly et al. "State of the Art Survey on MRI Brain Tumor Segmentation" Magnetic Resonance Imaging, vol. 31, No. 8, Jun. 19, 2013.
European Patent Office, International Search Report and Written Opinion for PCT/EP2013/073053 dated Jun. 27, 2014.

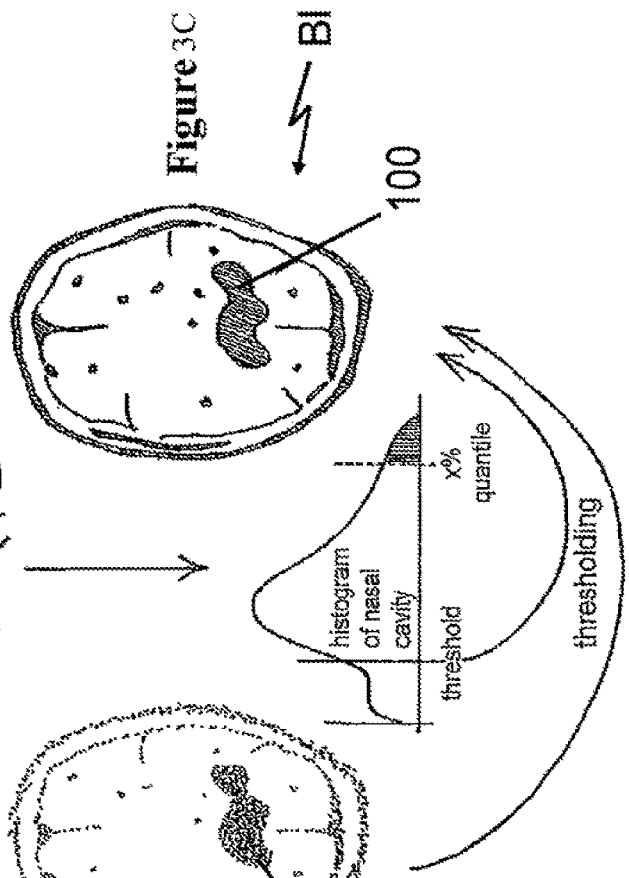

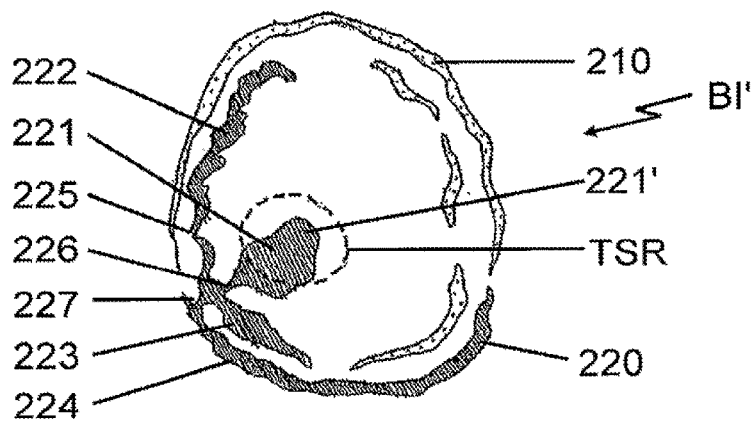
Figure 4
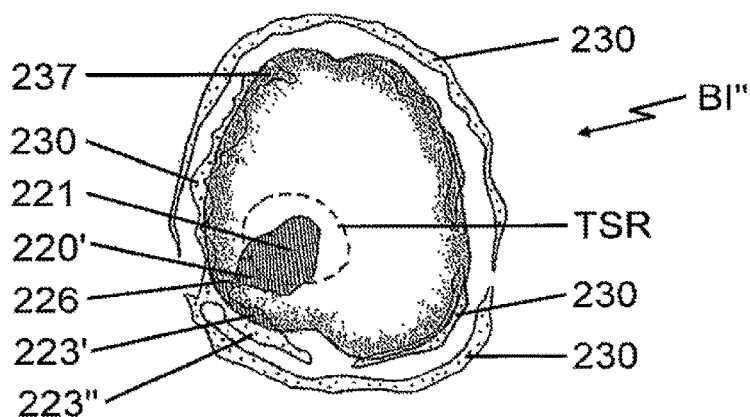
Figure 5
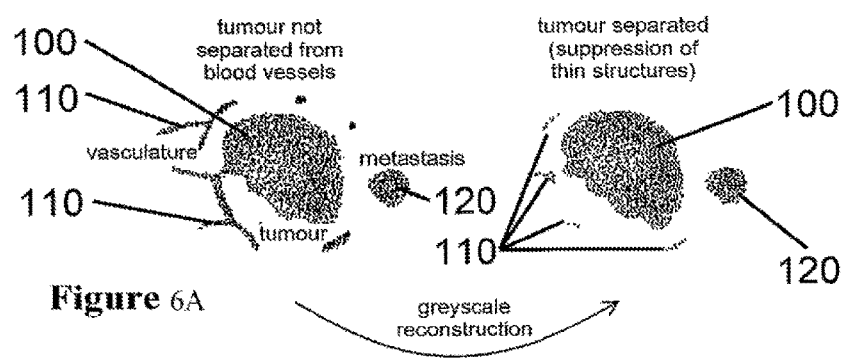
Figure 6A
Figure 6B slice -2 slice -1 slice 0 slice +1 slice +2

DETERMINATION OF ENHANCING STRUCTURES IN AN ANATOMICAL BODY PART

The present invention relates to the determination of enhancing structures (referred to as "enhancing structures of interest" or "structures of interest" for short, which are in particular tumours, metastases, etc.) within an anatomical body part. The determination is based on images acquired by a medical imaging method using a contrast agent.

The terms used in the application are defined in a separate section entitled "Definitions".

The structures of interest as mentioned above are in particular structures which accumulate the contrast agent. An example of such a structure of interest is in particular a tumour. Accordingly, "tumour" is also used, merely by way of example, for "structure of interest" in the following. Other examples of structures of interest include a metastasis and a nidus of malformations in arterial or venous structures.

With respect to the technical background of the invention, reference is made in particular to the following paper:

Kanaly, C. et al.: "A Novel Method for Volumetric MRI Response Assessment of Enhancing Brain Tumor" in PLOS ONE (an online publication) 6(1), 2011.

The abstract of the aforementioned paper reads as follows:

"Current radiographic response criteria for brain tumors have difficulty describing changes surrounding postoperative resection cavities. Volumetric techniques may offer improved assessment, however usually are time-consuming, subjective and require expert opinion and specialized magnetic resonance imaging (MRI) sequences. We describe the application of a novel volumetric software algorithm that is nearly fully automated and uses standard T1 pre- and post-contrast MRI sequences. T1-weighted pre- and post-contrast images are automatically fused and normalized. The tumor region of interest is grossly outlined by the user. An atlas of the nasal mucosa is automatically detected and used to normalize levels of enhancement. The volume of enhancing tumor is then automatically calculated. We tested the ability of our method to calculate enhancing tumor volume with resection cavity collapse and when the enhancing tumor is obscured by subacute blood in a resection cavity. To determine variability in results, we compared narrowly-defined tumor regions with tumor regions that include adjacent meningeal enhancement and also compared different contrast enhancement threshold levels used for the automatic calculation of enhancing tumor volume. Our method quantified enhancing tumor volume despite resection cavity collapse. It detected tumor volume increase in the midst of blood products that incorrectly caused decreased measurements by other techniques. Similar trends in volume changes across scans were seen with inclusion or exclusion of meningeal enhancement and despite different automated thresholds for tissue enhancement. Our approach appears to overcome many of the challenges with response assessment of enhancing brain tumors and warrants further examination and validation."

The object of the present invention is to provide a more robust determination of the structure of interest, wherein the present invention in particular allows the influence of the user on the final determination of the structure of interest to be reduced. Determining the structure of interest in particular involves determining spatial information of the structure of interest, in particular its geometry and/or position. The present invention in particular enables the structure of interest to be automatically determined.

Further background information, in particular with respect to the technique (which can be used to implement the present invention), is described in the following documents:

U.S. Pat. No. 8,280,133 B2, being the document "Method and System for Brain Tumor Segmentation in 3D Magnetic Resonance Images" by Wels et al.

U.S. Pat. No. 7,995,825 B2, being the document "Histogram Segmentation of FLAIR Images" by Jack et al.

US 2007/0064983 A1, being the document "Method for Automatically Detecting Nasal Tumor" by Huang et al.

WO 03/009214 A1, being the document "System and Method for Quantifying Tissue Structures and their Change over Time" by Tamez-Pena et al.

Vincent, L.: "Morphological Grayscale Reconstruction in Image Analysis: Applications and Efficient Algorithms" in IEEE Transactions on image Processing, Vol. 2, No. 2, pages 176-201, April 1993.

The present invention relates more generally to the field of medicine, in particular to the field of processing medical image data (also referred to as "medical images" or simply "images") acquired by means of medical imaging methods (see definition below). The above-mentioned object is solved by the subject-matter of any appended independent claim. Advantages, advantageous features, advantageous embodiments and advantageous aspects of the present invention are disclosed in the following and contained in the subject-matter of the dependent claims. Different advantageous features can be combined in accordance with the invention wherever technically expedient and feasible. Specifically, a feature of one embodiment which has the same or a similar function to another feature of another embodiment can be exchanged with said other feature, and a feature of one embodiment which adds an additional function to another embodiment can in particular be added to said other embodiment.

In the following, advantageous features and advantageous embodiments of the present invention are described.

The present invention is in particular directed to a data processing method for determining a structure of interest, in particular one or more structures of interest. The structure of interest is determined within an anatomical body part. "Determining the structure of interest within the anatomical body part" in particular means "determining an image of the structure of interest within an image of the anatomical body part", i.e. the present invention is in particular directed to the processing of image data acquired by medical imaging methods in order to determine spatial information concerning the structure of interest. The term "spatial information" encompasses the position and/or geometry (shape and/or size) of at least one enhancing structure of interest within the anatomical body part, in particular relative to the anatomical body part. The medical image used for determining the structure of interest is in particular a processed medical image which is preferably generated by applying the data processing method of the present invention to an enhanced image and a non-enhanced image, as described below. The processed medical image is in particular a processed binary image as described below, wherein the binary image is processed by a region-growing algorithm as described below.

The structure of interest has the property of exhibiting an enhanced signal in an image of the anatomical body part generated by the medical imaging method using a contrast agent, i.e. the enhancement of the signal is caused by the contrast agent accumulated in the structure of interest. In this regard, determining a structure of interest encompasses and in particular does not exclude determining other enhancing structures of interest (spatially distant from the first structure of interest) within the same anatomical body part in accordance with the present invention, in particular parallel or sequential to determining the enhancing structure of interest. The term "enhancing structure of interest" is therefore to be interpreted as meaning "at least one enhancing structure of interest".

The anatomical body part is a part of a human or animal body. The parts are in particular parts shown in an anatomical atlas and can for example be organs or other anatomical parts such as the head.

In accordance with one step of the data processing method, an image referred to as an "enhanced image" of the anatomical body part is acquired. Specifically, the enhanced image is acquired by acquiring data which describe the enhanced image and which are referred to as "enhanced image data". The acquired enhanced image has been obtained by using a medical imaging method and optionally subjecting the image generated by the medical imaging method to further image processing (see for example the application of a spatial filter as described below), in particular in order to suppress structures which are unlikely to be related to the structure of interest and/or in order to suppress inhomogeneities (see for example the section on "inhomogeneity correction" below). The medical imaging method has been performed using the contrast agent, as mentioned above. The contrast agent is in particular used by administering it to a patient (within whom the anatomical body part is situated), in particular before starting to generate the enhanced image by means of the medical imaging method. The structure of interest exhibits an enhanced signal in the enhanced image, wherein the term "enhanced" in particular means that the signal intensity deviates from the signal intensity obtained when the same medical imaging method is performed without using the contrast agent. This deviation is in particular above the average variation exhibited by a non-enhanced signal in the image.

In accordance with another step of the present invention, which can be performed before or after the aforementioned step, an image referred to as a "non-enhanced image" is acquired. Specifically, data which are referred to as "non-enhanced image data" and describe the non-enhanced image are acquired. The non-enhanced image is obtained by performing a medical imaging method and optionally also further image processing such as for example the inhomogeneity correction mentioned above and described further below. The medical imaging method is in particular the same medical imaging method as that mentioned above with respect to generating the enhanced image, except that the medical imaging method does not use the contrast agent in this case. This means in particular that the contrast agent is not administered to the patient before the non-enhanced image is obtained.

In accordance with another step of the data processing method, a spatial correlation between the enhanced image and the non-enhanced image is established. The enhanced image and non-enhanced image which have been spatially correlated with respect to each other are referred to as the spatially correlated enhanced image and spatially correlated non-enhanced image, respectively. The enhanced image and non-enhanced image are in particular registered with respect to each other. To this end, a common reference system for the enhanced image and non-enhanced image is preferably created. Preferably, the images are spatially correlated, in particular registered, by means of image fusion methods (see definition below). In particular, rigid or elastic image fusion is performed. In this case, a common reference system is established, i.e. sub-regions of the spatially correlated enhanced image and the spatially correlated non-enhanced image which represent the same sub-region of the anatomical body will have a similar and in particular identical position and/or geometry in the common reference system. These sub-regions are referred to as "corresponding sub-regions". Accordingly, voxels of the spatially correlated enhanced image and the spatially correlated non-enhanced image (and of the normalised difference image, see below) which represent the same part of the anatomical body and have a similar and in particular identical position in the common reference system are referred to as "corresponding voxels". Preferably, all the voxels of the spatially correlated enhanced image and the spatially correlated non-enhanced image which represent the same part of the anatomical body have a similar and in particular identical position in the common reference system.

In accordance with another step of the data processing method, an image referred to as a "normalised difference image" is determined. As the term "normalised difference image" implies, this image is determined by performing a normalising operation and a difference operation. Specifically, the intensity distribution of the voxels of the enhanced image and the intensity distribution of the voxels of the non-enhanced image are normalised with respect to each other in order to render the intensities comparable. This normalising operation is performed on the basis of intensities, in particular intensity distributions, within sub-regions of the enhanced image and non-enhanced image which are comparable to each other and preferably comprise sub-regions referred to as "non-enhanced sub-regions".

To this end, the non-enhanced sub-regions are acquired, preferably before the normalised difference image is determined. In particular, a non-enhanced sub-region is acquired in the enhanced image, and another non-enhanced sub-region is acquired in the non-enhanced image. These non-enhanced sub-regions are preferably sub-regions which do not exhibit an enhanced signal. The sub-regions can be selected by an operator or can be automatically determined, for example by comparing the enhanced image with the non-enhanced image with respect to its local intensity distribution. The non-enhanced sub-region of the enhanced image preferably has the same position and/or geometry as the non-enhanced sub-region of the non-enhanced image in a common reference system obtained in the spatial correlation step, i.e. the non-enhanced sub-region of the enhanced image and the non-enhanced sub-region of the enhanced image are corresponding sub-regions. The sub-region can be determined either by a user or automatically. If automatically determined, the intensity distribution in the enhanced image is in particular analysed in order to identify a sub-region with a standard deviation in its intensity and/or an average intensity which is lower than the average standard deviation and/or in order to identify a sub-region with an average intensity which is lower than the average intensity in a plurality of sub-regions of the enhanced image. Alternatively or additionally, symmetry properties of the anatomical body parts can be used to automatically determine the non-enhanced sub-region, as explained below.

The normalising operation can be performed by adjusting the intensity distribution within the non-enhanced sub-region of the enhanced image with respect to the intensity distribution within the non-enhanced sub-region of the non-enhanced image. This can in particular be achieved by adjusting the intensity distribution in the (spatially correlated) enhanced and/or non-enhanced image such that the average intensity in the respective (corresponding) non-enhanced sub-regions is made equal. This can for example be achieved by adding or subtracting a constant intensity value from the intensities of (all) the voxels of the (spatially correlated) enhanced and/or non-enhanced image, such that the average intensity in the respective (corresponding) non-enhanced sub-regions is made equal. In this way, the (spatially correlated) normalised enhanced image and the (spatially correlated) normalised non-enhanced image (also referred to as the "normalised spatially correlated enhanced image" and the "normalised spatially correlated non-enhanced image") can be obtained. An embodiment of a normalising operation is described in more detail in the detailed description of embodiments below. The term "average" as used here means in particular the mean, mode or median. Once the spatially correlated enhanced image and the spatially correlated non-enhanced image have been normalised with respect to each other, in particular by applying a normalising operation to the intensities of the voxels of at least one of these two images (i.e. the enhanced image and/or the non-enhanced image), a difference operation is preferably performed on the normalised spatially correlated enhanced image and the normalised spatially correlated non-enhanced image in order to determine an image which is then referred to as the "normalised difference image", in particular by subtracting the intensities of corresponding voxels from each other and assigning the results of the subtractions as intensities to corresponding voxels of the normalised difference image.

The structure of interest occupies a sub-region in the enhanced image which in particular exhibits a signal intensity in the enhanced image which significantly differs from the signal intensity exhibited in the corresponding sub-region (within the common reference system) in the non-enhanced image. The normalised difference image is intended to emphasise the differences in signal intensity. Thus, the normalised difference image allows the sub-regions which are candidates for the structure of interest to be identified. In order to identify the structure of interest, another step is preferably performed which involves acquiring a condition for the intensity (referred to as the "intensity condition"). If this condition is fulfilled, then there is a greater likelihood that the voxels in the sub-regions in the normalised difference image (or in an image obtained by processing the normalised difference image, for example by using the aforementioned spatial filter) are voxels of the structure of interest. One step of the data processing method therefore preferably involves acquiring an intensity condition for differentiating between structures of interest and other structures which do not exhibit an enhanced signal (in the enhanced image and/or the normalised difference image or processed normalised difference image). The intensity condition can in particular be such that it is fulfilled if the intensity of voxels is above a predetermined threshold. The step of acquiring and applying the intensity condition does not exclude the possibility of one or more other conditions also being acquired and applied, i.e. at least one intensity condition (see below) is acquired and applied.

A step of "determining a binary image on the basis of the intensity condition and the normalised difference image" in particular involves applying the intensity condition to the normalised difference image or to a processed normalised difference image, wherein processing the normalised difference image in particular involves applying the spatial filter. In accordance with one embodiment, therefore, the normalised difference image is subjected to a spatial filter (i.e. "processing") which suppresses structures which are unlikely to relate to the structure of interest. The spatial filter can in particular be designed such that thin and lengthy structures such as arteries or isolated high-intensity voxels (which are due to statistical noise) can be suppressed, i.e. in accordance with one embodiment (explained in more detail further below), the data processing method comprises the additional steps of acquiring a spatial filter and then applying the spatial filter to the normalised difference image, before performing the subsequent additional step described in the following paragraph.

In accordance with this additional step, the intensity condition is used to determine a binary image from the normalised difference image or the processed normalised difference image, i.e. such that voxels in the determined binary image represent digital information only (for instance, "YES" or "NO"). This means that the only information for each voxel contained in the binary image is that of whether the voxel represents an enhanced signal intensity or a non-enhanced signal intensity, i.e. whether the voxel fulfils the intensity condition or does not fulfil the intensity condition.

In accordance with another step, the binary image is used in order to acquire a sub-region within the binary image which is referred to as the "start region". The start region can be acquired by receiving data which describe the position and/or geometry (shape and/or size) of the start region (for example via a user input) or by automatically determining the start region in the way described below. The start region is known or assumed to comprise at least some of the structure of interest. This knowledge can for example be garnered from a longitudinal study of the tumour development within the patient, for example in the form of a sequence of images over a longer period of time which correspondingly show the growth of a tumour. The start region can be selected by a user or automatically identified by a program, in particular in such a way that the start region encompasses the tumour or at least a major part of it. The start region can for example be automatically determined using symmetry properties of the anatomical body parts and/or significant deviations between the intensity in the sub-region which is a candidate for the start region and the intensity in other sub-regions, as discussed below.

In accordance with a particular feature of the present invention, the start region does not represent a strict borderline for the structure of interest but rather defines a region from which to start a flexible and elaborate process for determining the structure of interest. This means that the process of determining the structure of interest in accordance with the present invention is not significantly dependent on the position and geometry of the start region (which may be selected differently by different users). This makes the process of the present invention particularly robust.

As indicated above, acquiring the start region does not represent the end point of the data processing method; instead, the image elements within the start region are then used for further processing. The image elements of the binary image which fulfil the intensity condition can be understood to represent "seed points" for this further processing. These image elements are accordingly referred to as "seed image elements". All the voxels within the start region of the binary image which fulfil the intensity condition(s) collectively represent a structure which is referred to as the "start structure".

In accordance with another step of the data processing method, the seed image elements are used to expand the start structure if (and in particular only if) certain conditions apply. Preferably, a so-called "region-growing algorithm" is applied in order to expand the start structure. The expanding start structure is referred to as the "growing structure". The aforementioned seed elements serve as seed points for the region-growing algorithm. The region-growing algorithm is designed to add one or more image elements of the binary image which fulfil the intensity condition to the growing structure if certain conditions apply. Image elements represented in the binary image which fulfil the intensity condition are referred to as "enhanced binary image elements". Enhanced binary image elements are added to the growing structure (only) if certain conditions are fulfilled. They are preferably added in steps, such that the growing structure grows progressively from the start structure into an enlarged growing structure. In particular, enhanced binary image elements added to the growing structure serve as additional seed points for the region-growing algorithm. Since the start structure represents the agglomeration of enhanced binary image elements within the start region, the added image elements are preferably outside the start region. The enhanced binary image elements are added to the growing structure (only) if certain conditions apply. One of these conditions is that an enhanced binary image element is only added to the growing structure if the enhanced binary image element is adjacent to the growing structure, wherein "adjacent" preferably means that the enhanced binary image element is a neighbouring image element of an enhanced binary image element which is already part of the growing structure, wherein "neighbouring" in turn means in particular that the voxel which represents the enhanced binary image element is preferably in contact via a corner (in a two-dimensional image) or edge (in a three-dimensional image) and/or via an edge (in a two-dimensional image) or a face (in a three-dimensional image) with an enhanced binary image element which is already part of the growing structure. Another condition, which has already been mentioned, is that the image element has to be an enhanced binary image element. As also already mentioned above, the image elements are added to the growing structure even if the enhanced binary image elements are outside the start region.

The growing procedure is performed in steps, as mentioned above, until the availability of enhanced binary image elements which fulfil at least the aforementioned conditions is exhausted. Other conditions, which are mentioned below, can also be applied, in particular in order to prevent the growing structure from "protruding" (or "leaking" and in particular undesirably spreading), while the region-growing algorithm is being applied, into regions in which the structure of interest is assumed or known to not be present, such as for example regions known or assumed to belong to a "non-habitat structure" as described below (and for example identified using a brain mask). This is explained in more detail further below. Alternatively or additionally, image elements which are unlikely to belong to the structure of interest can be removed from the final growing structure using particular procedures, as described in more detail further below (see the section on "brain mask"), in order to process the final growing structure, i.e. determining the structure of interest on the basis of the final growing structure encompasses equating the structure of interest with the final growing structure or further processing the final growing structure (for example by applying the brain mask) and then equating the processed final growing structure with the structure of interest. The structure obtained following this removing operation is then determined to be the structure of interest, i.e. the final growing structure is used as a basis for determining the structure of interest in that it is either identified as being the structure of interest or is used as the starting point for a particular procedure, the result of which is identified as the structure of interest.

As mentioned above, the growing structure can be prevented from protruding as the region-growing algorithm is applied by enforcing at least one other condition. In accordance with one embodiment, this other condition is used to prevent the growing structure from spreading beyond a habitat structure (such as for example the white matter in a brain), i.e. from protruding into a non-habitat structure. The habitat structure is a structure in which the structure of interest is known or assumed to be contained, and a non-habitat structure is a structure in which the structure of interest is known or assumed to not be contained.

Any undesirable spread of the growing structure can also be reversed by removing any image elements which do not belong to a habitat structure from the final growing structure. Alternatively or additionally, a condition can be enforced whereby image elements which belong to a non-habitat structure are not added. Alternatively or additionally, image elements which belong to a non-habitat structure can be removed from the final growing structure. If image elements are removed from the final growing structure, then the final growing structure which has been subjected to the removing operation is preferably deemed to represent the structure of interest.

In accordance with another embodiment, the method comprises a step of acquiring data which are referred to as "property data" and describe spatial and/or representational properties of the habitat structure and/or the non-habitat structure. Spatial properties can comprise information on the relative position of the habitat structure and/or non-habitat structure relative to anatomical structures represented in a medical image. In particular, the relative position is described by the spatial property data. The relative position of the skull is for example described relative to the white matter. The spatial properties preferably comprise information on the geometry of the habitat structure and/or non-habitat structure, such as for example the typical shape of a skull. The property data can be described by an anatomical atlas which describes the spatial properties of the habitat structure and/or the non-habitat structure. The representational properties in particular comprise information on the absolute intensity of the habitat structure and/or non-habitat structure in a medical image and/or information on the relative intensity of the habitat structure and/or non-habitat structure relative to anatomical structures represented in the medical image. The relative intensity is in particular described in terms of the medical imaging method used to generate the medical image (for example, the type of MRI, the magnetic field strength, etc.). If the medical imaging method uses x-ray (such as for example CT), the representational properties also in particular comprise information on absolute intensities (for example in Hounsfield units). The property data in particular describe the properties of the habitat structure and/or non-habitat structure in the enhanced image and/or non-enhanced image and/or normalised difference image. The property data are preferably used to identify the habitat structure and/or non-habitat structure, i.e. the spread of the growing structure can be prevented or reversed on the basis of the property data, by determining whether an image element belongs to the habitat structure or the non-habitat structure. The aforementioned enhanced image and/or non-enhanced image is/are in particular a spatially correlated enhanced image and/or non-enhanced image, respectively. Due to this spatial correlation, an image element identified as belonging to the habitat structure or the non-habitat structure has a defined position in the common reference system. This means that the corresponding image element in the binary image can also be identified as belonging to the habitat structure or the non-habitat structure, respectively. Generally, there is preferably a spatial correlation between the image elements of the enhanced image, the non-enhanced image, the normalised difference image and the binary image. This enables information on whether an image element in one of the images belongs to a habitat structure and/or a non-habitat structure to be transferred to a corresponding image element in another of the images. Preferably, there is a bijective positional relationship between the image elements (voxels) of the aforementioned images.

The geometrical properties of the non-habitat structure can for example correspond to the geometrical properties of a vascular system and/or can correspond to single image elements which exhibit an intensity which represents a spike in the intensity distribution of the surrounding image elements, i.e. which deviates from the average intensity by more than a defined threshold which is a function of the standard deviation of the variation in intensity. If, for example, the intensity of the image element deviates by more than two standard deviations from the average intensity in its surroundings (which can be defined to comprise a predefined number of image elements), then it is assumed to represent a statistical spike in the intensity distribution. To this end, the normalised difference image is preferably processed, before the binary image is determined, in order to change the intensity of image elements which belong to structures exhibiting the aforementioned geometrical properties and/or the aforementioned representational properties (such as for example intensity spikes). To this end, a spatial filter is preferably applied which is in particular a filter which performs greyscale reconstruction (see in this respect the above-mentioned paper by L. Vincent). The intensity of the image elements is preferably changed such that there is a greater likelihood that the changed intensity does not fulfil the intensity condition, in particular if the image element with the changed intensity belongs to a non-habitat structure and/or does not belong to a habitat structure. The changed intensity is in particular closer to the intensity threshold or passes the intensity threshold (as compared to the situation before the intensity was changed) if the intensity condition was fulfilled before the intensity was changed. If the image element has been identified as belonging to a structure which has geometrical properties similar to a vascular system and/or if the image element represents an intensity spike, then it is in particular assumed that it does not belong to a habitat structure and/or that it does belong to a non-habitat structure. By changing the intensity value of such image elements in such a way that they do not fulfil the intensity condition, it is possible to prevent the growing structure from spreading into the parts occupied by these image elements when the region-growing algorithm is applied.

In accordance with another embodiment, which is in particular based on the aforementioned embodiments, the undesirable spread of the growing structure is prevented by applying a mask to a medical image. The mask is preferably constituted to extract parts of the image which belong to the habitat structure and/or to block parts of the medical image which belong to the non-habitat structure in order to only apply the region-growing algorithm to image elements which belong to the habitat structure and/or to block the participation of image elements which belong to the non-habitat structure in the region-growing algorithm. The aforementioned medical image is in particular the non-enhanced image and/or the enhanced image and/or the normalised difference image (and/or the binary image). The enhanced image and/or the non-enhanced image is in particular the spatially correlated enhanced image and/or the spatially correlated non-enhanced image, respectively. The mask is preferably based on spatial and/or representational properties as described by the property data. An example of such a mask is the brain mask described in more detail in the detailed description of the embodiments further below. The mask can be generated automatically or by user interaction.

In accordance with another embodiment, an anatomical atlas is used to segment the habitat structure and/or non-habitat structure in a medical image. The medical image is preferably the (spatially correlated) non-enhanced image and/or the (spatially correlated) enhanced image and/or the normalised difference image. The anatomical atlas is in particular an example of property data and describes spatial and/or representational properties of the habitat structure and/or the non-habitat structure.

As already indicated above, the aforementioned undesirable spread of the growing structure is prevented by blocking image elements represented in the binary image from participating in the region-growing algorithm, such that only image elements determined to belong to the non-habitat structure participate. These image elements are preferably blocked before the region-growing algorithm is applied, for example by setting the intensity of these image elements to a value which does not fulfil the intensity condition. Alternatively or additionally, the image elements can be blocked from participating in the region-growing algorithm while it is being applied, by prohibiting these image elements from being added to the growing structure.

Alternatively or additionally, the participation of image elements in the region-growing algorithm can be restricted to particular image elements. These particular image elements are preferably those which have been determined to belong to the habitat structure. This means that region-growing can only be performed within the habitat structure. This is preferably implemented before or while the region-growing algorithm is applied, for example by only allowing image elements to fulfil the intensity condition(s) if they belong to the habitat structure, or by extracting the image elements which belong to the habitat structure before applying the region-growing algorithm and then applying the region-growing algorithm only to these extracted image elements.

Alternatively or additionally, image elements which have already become part of the growing structure, in particular part of the final growing structure, can be removed, in particular after the final growing structure has been determined, if they fulfil certain conditions, such as for example in particular if they belong to the non-habitat structure. This removing operation is preferably performed before the growing structure is determined to be the structure of interest.

In accordance with another embodiment, the non-enhanced sub-region is determined on the basis of a representation of a part (sub-region) of the habitat structure, i.e. the habitat structure is for example identified using an anatomical atlas and the intensity distribution within the sub-region is then analysed. If the peaks of the intensity distribution do not indicate an enhanced signal, and in particular if they do not exceed a predefined intensity level, then it is assumed that the sub-region does not include any potential candidate for a structure of interest and it is determined to be a non-enhanced sub-region.

In accordance with another embodiment, the start region is determined on the basis of a symmetry analysis of the anatomical body part. If the anatomical body part exhibits symmetry properties, such as for example a brain which comprises a left and right hemisphere, then deviations from the symmetry properties within sub-regions can be used as an indication that a structure of interest is present in said sub-region. If, in particular, the anatomical body part (including the structure of interest) comprises a mid-sagittal plane which divides the anatomical body part into a first and a second part, the symmetry properties of the anatomical body part can be used to determine the start region. If, in particular, the structure of interest is located in one half (a first part) of the anatomical body part, then it is unlikely that another structure of interest will also be found, symmetrically located, in the other (second) part. It is therefore likely that there will be a deviation in the symmetry properties between the left and right half of the anatomical body part. In both parts, there is a habitat structure within which the structure of interest may be located. In order to determine the start region, the symmetry properties of the anatomical part are therefore analysed by comparing spatial and/or representational properties of the left and right half of the anatomical body part with respect to a deviation in symmetry. Before the analysis with respect to symmetry is performed, the three-dimensional medical image is preferably processed in order to cut it into two-dimensional layers. The two-dimensional layers are preferably cut such that the symmetry plane (for example, the mid-sagittal plane) passes perpendicularly through the layers. The layers are then respectively analysed with respect to their symmetry, i.e. the left half is compared with the right half. The higher the deviation in the spatial (in particular geometrical) and/or representational (in particular intensity) properties, the greater the certainty that the corresponding layer is not symmetrical.

As mentioned above, the intensity condition is preferably acquired. The intensity condition can for example be acquired manually via a user input or also, in accordance with one embodiment, automatically on the basis of the enhanced image. To this end, an enhanced sub-region which represents a calibration structure in the enhanced image is preferably determined. The calibration structure is in particular not the structure of interest. Nevertheless, the intensity of the calibration structure as represented in the (spatially correlated) enhanced image differs significantly from the intensity of the calibration structure in the (spatially correlated) non-enhanced image. This difference in intensity is preferably known or assumed to be reproducible, such that the difference in intensity can be used as a basis for determining the intensity condition, i.e. the intensity, in particular the intensity distribution within the calibration structure as represented in the enhanced image, is used as a basis for determining the threshold.

In accordance with one embodiment, the tumour can comprise metastases which are spatially distinct from the main body of the tumour. In this case, the method of the present invention preferably does not necessarily include the following steps (i.e. the following steps, mentioned in Claim 1, are not essential):

acquiring a sub-region within the binary image which is referred to as the start region and which is known or assumed to comprise at least a part of the structure of interest;

determining image elements of the binary image within the start region which fulfil the intensity condition, wherein these image elements are referred to as seed image elements and collectively represent a structure which is referred to as the start structure;

determining a structure referred to as the final growing structure, on the basis of the binary image using a region-growing algorithm which starts with the seed image elements which serve as seed points for the region-growing algorithm, wherein the region-growing algorithm is constituted to add image elements represented in the binary image to the start structure, which is then referred to as the growing structure and is equal to the start structure before the image elements are added, wherein the added image elements serve as additional seed points for the region-growing algorithm, and the region-growing algorithm is constituted to add image elements of the binary image to the growing structure if at least the following conditions are fulfilled:

the image elements represented in the binary image are adjacent to the growing structure; and the intensity of the image elements of the binary image represent an enhanced signal intensity, the image elements being added until no further image elements of the binary image are to be added to the growing structure in accordance with the region-growing algorithm, wherein the growing structure is then the final growing structure; and determining the structure of interest on the basis of the final growing structure.

This means that in this case, after the binary image has been determined, steps other than the aforementioned steps can be performed in order to determine the exhibited metastases. The following steps can of course be combined with the aforementioned steps in order to determine both the tumour and the spatially distinct metastases. The metastases generally have particular geometrical properties which are preferably used in order to determine the metastases.

Data referred to as metastasis geometry data are preferably acquired. These metastasis geometry data describe geometrical properties of the metastases and in particular the geometrical properties of the metastases in image layers. The binary image is preferably a three-dimensional image which comprises a plurality of two-dimensional image layers. The image layers respectively comprise a plurality of pixels. The metastasis geometry data describe the geometrical properties of the metastases in the image layers. These geometrical properties include in particular relative geometrical properties which describe the relative variation in the geometry of a metastasis of one image layer with respect to another image layer and in particular from one image layer to an immediately adjacent, i.e. neighbouring, image layer.

Preferably, a set of adjacent (in particular neighbouring) enhanced image elements is within at least one of the image layers, preferably in several neighbouring image layers. The set of adjacent image elements is preferably integrally closed and preferably set apart from other sets and/or other image elements which represent the enhanced signal intensity. The sets are then analysed with respect to their geometrical properties in the image layers, in particular with respect to their two-dimensional properties in the respective image layers. A set is preferably determined to represent a metastasis if it exhibits two-dimensional geometrical properties which match the geometrical properties described by the metastasis geometrical data. The required geometrical property may for example be that the borderline of the set exhibits a shape which is similar to a circle.

In accordance with another embodiment, which is in particular based on the aforementioned embodiment, the sets are analysed with respect to their relative geometrical properties when comparing one image layer with another image layer. A set within one image layer is referred to as a metastasis slice. Preferably, the metastasis geometry data describe how a set is identified as a metastasis if it exhibits at least one of the features described in the following. These features are in particular features which reflect the fact that the combined metastasis slices are similar to a spherical shape.

In accordance with one geometry feature, the metastasis slices are present in adjacent (neighbouring) image layers. The metastasis slices are in particular described as being arranged one above the other in adjacent (neighbouring) image layers. The metastasis slices are in particular arranged concentrically. Preferably, the metastasis geometry data describe how a larger metastasis slice encompasses smaller metastasis slices in the other, adjacent (neighbouring) image layers if viewed in a direction perpendicular to the plane of the image layer. Preferably, the metastasis geometry data describe how the size of a metastasis slice between two other metastasis slices (where all three are arranged one above the other) preferably differs in that the size of the middle metastasis slice is larger than at least one of the other two metastasis slices. This condition represents the spherical shape usually observed in metastases. In particular, the middle metastasis slice represents a maximum size or a medium size between the sizes of the other two neighbouring (outer) metastasis slices. If viewed in a direction perpendicular to the image layers, the larger of the neighbouring metastasis slices preferably encompasses the smaller neighbouring metastasis slice. The metastasis geometry data preferably describe how at least one and in particular only one of the metastasis slices arranged one above the other is larger than the two neighbouring metastasis slices.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, in particular electrical, in particular technically generated) signal wave, in particular a digital signal wave, carrying information which represents the program, in particular the aforementioned program, which in particular comprises code means which are adapted to perform any or all of the method steps described herein.

The present invention is also directed to a medical image processing system for determining a structure of interest. The medical image processing system comprises at least one analytical device for generating medical images of an anatomical body part by means of a medical imaging method. The medical image processing system also comprises a computer which is constituted to process the generated images by running the aforementioned program. The computer comprises a program storage medium on which the aforementioned program is loaded. Running the program allows a structure of interest to be determined on the basis of the generated images.

Additional features of the present invention are disclosed in the following detailed description.

FIG. 1 schematically shows the steps of an embodiment of the method of the present invention.

FIGS. 2A-C illustrate some of the steps of the method of the present invention.

FIGS. 3A-D illustrate some of the steps of the method of the present invention.

FIG. 4 illustrates the so-called protrusion which may occur during region growing.

FIG. 5 illustrates how protrusion is suppressed.

FIGS. 6A-B illustrate how protrusion is suppressed by greyscale reconstruction.

FIGS. 7A-E illustrate how a metastasis is detected.

Figure 8:
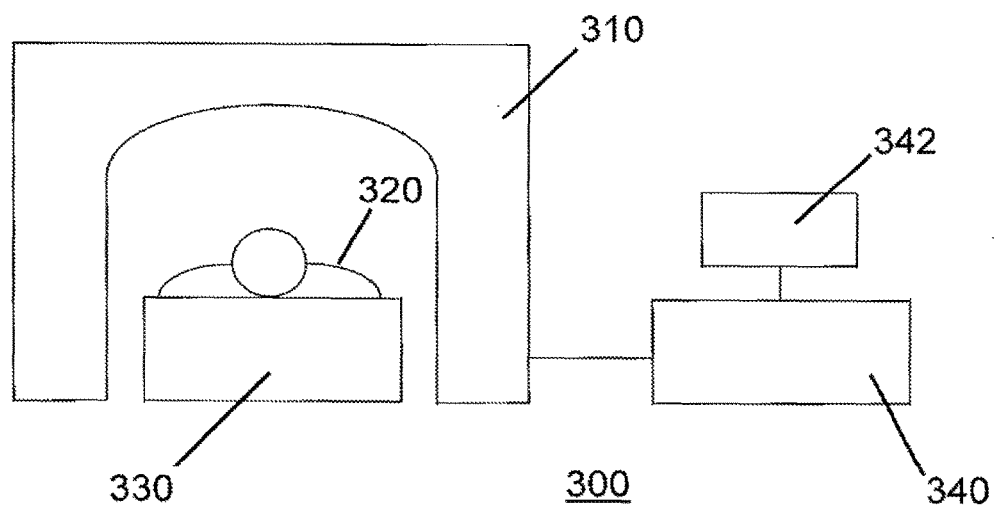

FIG. 8 schematically shows a medical image processing system.

Figure 1:
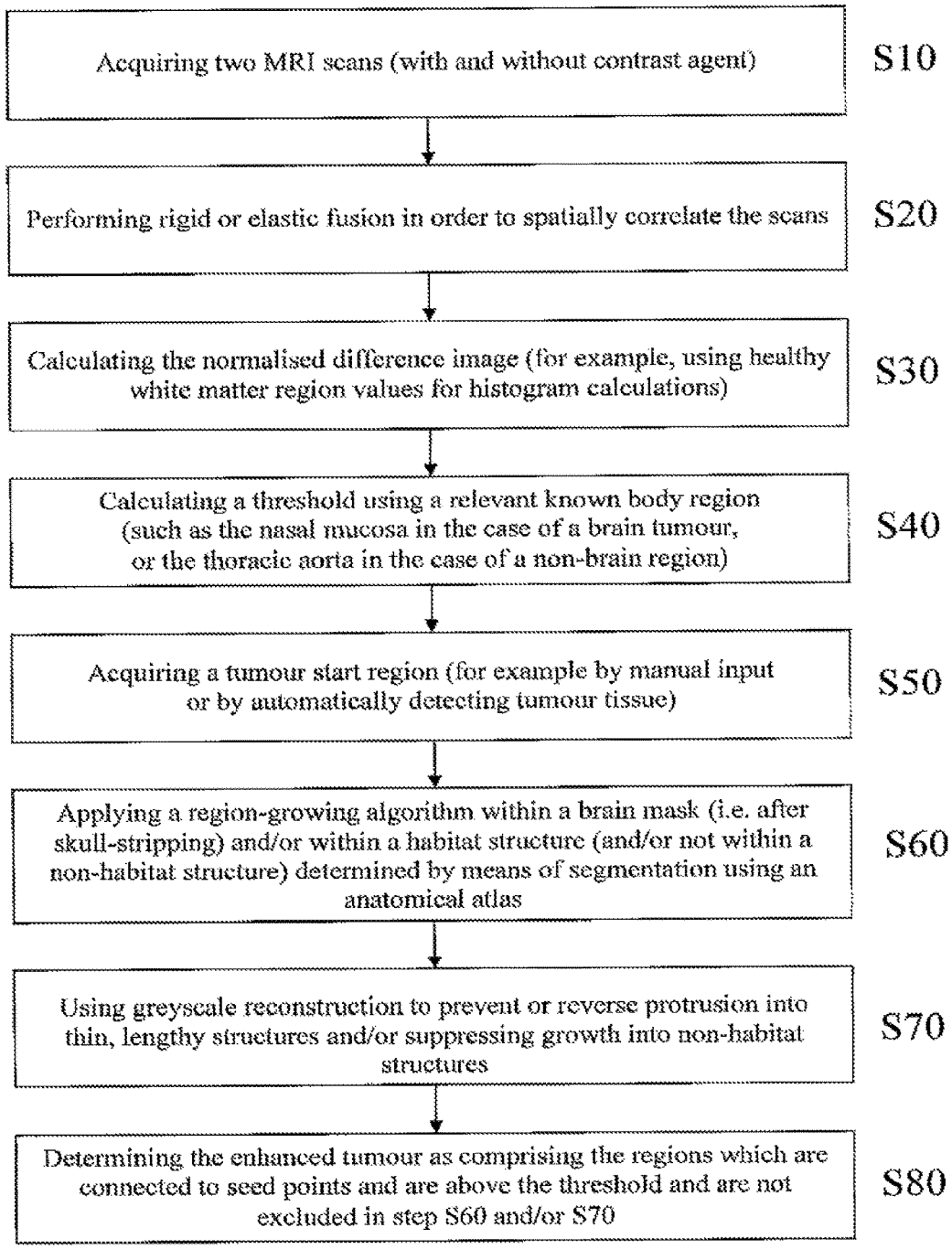

FIG. 1 schematically shows the steps of an embodiment of the data processing method of the present invention. In a first step S10, two images are acquired. One of the two images (shown in FIG. 2A) is generated by administering a contrast agent to the patient in order to improve the visibility of particular internal body structures which are of interest and therefore referred to as "structures of interest". In the following, the structure of interest is assumed for the sake of example to be a tumour. The structure of interest is situated within an anatomical body part of the patient. The medical imaging method is in particular a magnetic resonance imaging method or x-ray computer tomography (CT) imaging method. In the example shown in FIG. 1, the resulting image (referred to as an enhanced image) is a T1-weighted image (also referred to as a T1-weighted scan). The T1-weighted scan generated using a contrast agent is denoted as "T1w+c" in FIGS. 2A-C.

Another image, which is a non-enhanced image, is also acquired in step S10. The non-enhanced image is generated without using a contrast agent. The non-enhanced image is in particular generated using a magnetic resonance imaging (MRI) method. The image is preferably of the same modality as the enhanced image, i.e. in the example of FIG. 1, the non-enhanced image is preferably also a T1-weighted image (also referred to as a T1-weighted scan).

In a following step S20, the non-enhanced image (also referred to as T1w−c, as for example in FIGS. 2A-C) and the enhanced image (T1w+c) are preferably spatially correlated, in particular registered, with respect to each other, preferably by means of image fusion. One particular result of spatial correlation is that the non-enhanced image and the enhanced image are described in a common reference system. The images can be three-dimensional or two-dimensional images, but are preferably three-dimensional images or sets (in particular stacks) of two-dimensional images (such as for example two-dimensional layers of voxels positioned one above the other as described with respect to FIGS. 7A-E) which describe two-dimensional features of the same three-dimensional structure (for example, the head) and which are in particular positioned one above the other. Preferably, rigid or elastic image fusion is selected, depending on the type of anatomical body part in question, as represented by the images. If, for example, the images represent the head of a patient (or part of it), then rigid image fusion is preferred in accordance with one embodiment. Elastic fusion is preferred for images representing extra-cranial body parts.

While performing image fusion or in a separate, either preceding or subsequent step, at least one of the enhanced image and the non-enhanced image is preferably transformed in such a way that there is a bijective assignment between the respective image elements (in particular, the voxels) of the enhanced image and the non-enhanced image once the transformation is complete. In the following, the image elements are referred to as voxels by way of example only. In particular, layers resulting from the images generated (by MRI) have a one-to-one correspondence once the transformation is complete. In order to achieve this bijective relationship (in particular, the one-to-one correspondence between the layers, in particular the voxels), an interpolation (for example, a cubic or spline interpolation) is preferably used to calculate the position of the voxels and/or the colour value (in particular, the intensity) assigned to the respective voxels, so that a one-to-one correspondence between the voxels can be established.

The acquired images have preferably already been processed in accordance with standard procedures to eliminate brightness variations due to the imaging method, such as for example intensity inhomogeneity in the case of MRI images, and in particular to adjust the brightness of anatomic structures belonging to the same class of tissue. These procedures in particular involve correcting inhomogeneity, as for example in an "RF inhomogeneity correction" or a "bias field correction". One such standard procedure is known as "N3".

In a following step S30, the normalisation difference image is preferably calculated. In the example shown in FIG. 2A, the MRI image is an image of the patient's head. The brain in particular is shown in the MRI image. A so-called "non-tumour region" (NTR in FIG. 2A) is preferably acquired (in particular selected) in both the enhanced image and the non-enhanced image. This region is encircled in FIG. 2A and used for the normalisation process. It is necessary to normalise MRI images in particular, since their intensity values are not normalised (unlike CT images). The non-tumour region is a region which does not exhibit an enhanced signal; in particular, the contrast agent has no effect on the intensity of voxels in the non-tumour region. The non-tumour region is an example of the "non-enhanced sub-region".

The non-tumour region can be selected by a user. In accordance with another embodiment, however, the non-tumour region is selected automatically, in particular in the case of a symmetrical anatomical body part such as the brain. The brain exhibits symmetrical properties. Preferably, tissue within which the tumour could be embedded is identified, for instance using an anatomical atlas. If the tumour is only present on one side of the brain (i.e. on one side of the mid-sagittal plane), then white matter (which is non-enhanced) situated in particular very distant from the suspected tumour region, in particular on the other side of the mid-sagittal plane, can be used as a non-tumour region. The white-matter region is in particular identified using an anatomical atlas. The non-tumour region can in particular be identified by detecting intensity and/or symmetry deviations between the two sides of the brain. The symmetry analysis is in particular performed on layers of the brain. The aforementioned steps can be performed automatically in order to automatically identify a region of interest and/or a non-tumour region.

Figures 2A, 2B, 2C:
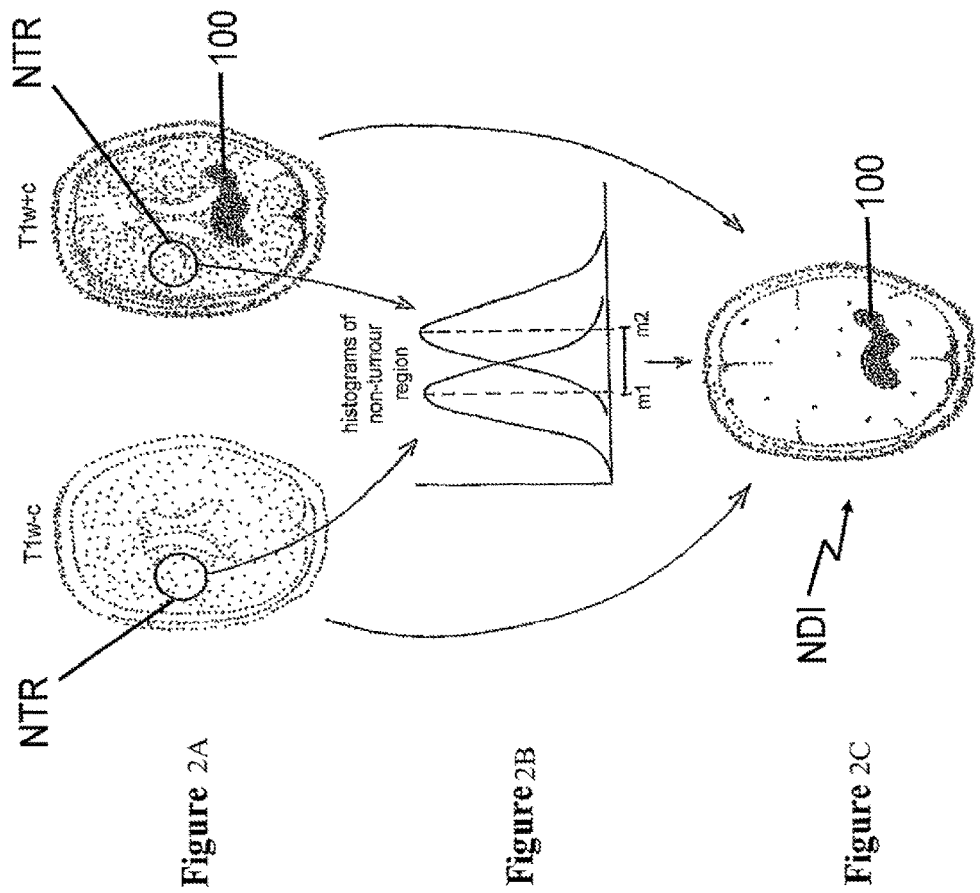

In a sub-step of step S30, the intensity distribution within the non-tumour region in the enhanced image and the intensity distribution within the non-tumour region in the non-enhanced image is analysed. The corresponding distribution is shown in FIG. 2B and denoted as "histograms of non-tumour region". An average intensity deviation between the two non-tumour regions is determined on the basis of these histograms, and the images are normalised on the basis of this average. Any kind of average, such as a mean, mode or median, can be used. In the example shown in FIGS. 2A-C, the average intensity—preferably, the mode (m1 and m2, as shown in FIG. 2B)—is determined for each of the intensity distributions (in particular, histograms).

In a subsequent sub-step of Figure S30, a normalised difference image (NDI in FIG. 2C) is determined by applying the following equation to each of the corresponding voxels of the enhanced image and the non-enhanced image, in order to calculate the intensity—referred to as "ID"—of the corresponding voxel of the normalised difference image, in particular based on the established one-to-one correspondence between the voxels of the enhanced and non-enhanced image:

$$ID = (I2 - A2) - (I1 - A1)$$

where I1 is the intensity of the voxel of the enhanced image or the non-enhanced image, but preferably the non-enhanced image, A1 is the average intensity value of this image (for example, the mode m1), I2 is the intensity of the corresponding voxel of the other image (the non-enhanced image or the enhanced image, but preferably the enhanced image) and A2 is the average intensity value of said other image (for example, the mode m2). The calculation is preferably performed for all (or most) of the voxels of the enhanced image and the respectively corresponding voxels of the non-enhanced image. In the example of FIG. 2C, m1=A1 and m2=A2. The normalised difference image exhibits an increase in contrast between non-enhanced image parts and enhanced image parts as compared to the enhanced image.

The equation is preferably applied in such a way that the resulting difference in the intensity of voxels representing the structure of interest (for example, a tumour) is positive. In the case of T1 images, the use of contrast agents generally results in an increase in intensity. In this case, therefore, I1 is preferably the voxel intensity of the non-enhanced image and I2 the voxel intensity of the enhanced image. However, it is also possible for the use of contrast agent to lower the signal intensity. This is in particular the case with T2 images which for example use barium sulphate as the contrast agent. In this case, I1 in the above-mentioned equation is preferably the voxel intensity of the enhanced image and I2 is preferably the voxel intensity of the non-enhanced image. If the intensity ID of a voxel of the normalised difference image becomes negative, then it is preferably set to zero.

Applying the above-mentioned equation to the voxels of the enhanced image and the non-enhanced image results in the normalised difference image shown in FIG. 2C. As can be seen from FIG. 2C, the visibility of the tumour 100 has been increased as compared to the visibility of the tumour 100 in the enhanced image (T1w+c) shown in FIG. 2A. In particular, the contrast between the non-enhanced region and the enhanced region is increased in the normalised difference image ("NDI") as compared to the enhanced image.

In order to further clarify which voxels exhibit an intensity caused by the contrast agent and which do not, an intensity condition—in particular, a threshold—is acquired in step S40 in order to be able to differentiate between voxel intensities caused by the contrast agent and voxel intensities not caused by the contrast agent. In accordance with one embodiment, such an intensity condition can be acquired by means of a user input. In accordance with another embodiment, the intensity condition can be determined by referring to a body region which exhibits a known and reliable intensity response to the contrast agent in an enhanced image. In the case of the head, in particular the brain and more particularly a brain tumour, one such corresponding region is in particular the nasal mucosa. In the case of non-brain regions, one such corresponding region is in particular the thoracic aorta.

FIG. 3A shows an enhancement of the surrounding tissue of the nasal cavity (denoted by the reference sign 110) due to the use of contrast agent. FIG. 3D shows the intensity distribution (in particular, a histogram) of the voxels representing the nasal cavity (i.e. the nasal mucosa). When determining the threshold, the voxels having the highest intensity values are preferably excluded. In accordance with a first embodiment, a predetermined percentage (x % quantile) of voxels is excluded, such that only voxels of lower intensities remain. The percentage of excluded (higher-intensity) voxels is preferably higher than 1%, in particular higher than 3%, and/or lower than 30%, in particular lower than 15% and more particularly lower than 7%.

In accordance with said first embodiment, the voxel having the highest intensity is determined from the remaining (non-excluded) voxels, and a threshold is determined on the basis of this intensity, as a predetermined percentage of the intensity of said voxel. This percentage is preferably higher than 10%, in particular higher than 20%, and/or preferably lower than 40%, in particular lower than 30%.

In accordance with a second embodiment, a percentage of voxels exhibiting the lowest intensities within the intensity distribution (FIG. 3D) is determined, and the threshold is set at the voxel exhibiting the highest intensity within these low-intensity voxels. This predetermined percentage is preferably higher than 10%, in particular higher than 20%, and/or preferably lower than 40%, in particular lower than 30%.

In accordance with another embodiment, the intensity condition is not described by an exact value in the form of a threshold but is instead defined by combining a threshold value with a noise function, wherein the value of the noise function is dependent on the position of the voxel.

FIG. 3B illustrates the normalised difference image NDI which is identical to that shown in FIG. 2C. The threshold determined in accordance with FIG. 3D) is applied to the normalised difference image NDI of FIG. 3B, i.e. to all the voxels of the image, in order to determine the binary image BI shown in FIG. 3C, i.e. each voxel in the binary image is determined as either representing an enhanced signal intensity or as not representing an enhanced signal intensity, hence the term "binary" image. In FIG. 3C), the voxels determined as representing an enhanced signal intensity (also referred to as "enhanced voxels") are shown in black. The tumour 100 in the binary image BI is therefore also shown in black. The voxels determined as representing a non-enhanced signal intensity (also referred to as "non-enhanced voxels") are shown in white.

Additional explanations with respect to steps S10 to S40 can be found in Kanaly, C. et al.: "A Novel Method for Volumetric MRI Response Assessment of Enhancing Brain Tumor" in PLOS ONE (an online publication) 6(1), 2011.

FIG. 4 shows another example of a binary image BI'. The enhanced voxels are enclosed by continuous lines. There are two types of enhanced voxels in FIG. 4. The dotted area 210 represents enhanced voxels, and the hatched area 220 also represents enhanced voxels. The non-enhanced voxels are shown in white. A dashed circular line surrounds a so-called tumour start region ("TSR" in FIG. 4) which is also referred to herein simply as the "start region". The tumour start region TSR is acquired in step S50 of the method shown in FIG. 1. The data which describe the position and geometry of the tumour start region in the binary image can be acquired by a user input or also automatically. If the anatomical body part (as represented in the binary image) has symmetrical properties, the image can be analysed for deviations from this symmetry. The parts of the image which deviate from the symmetrical properties can be identified as a tumour start region. This procedure is preferably applied if the tumour is only present in one half of the symmetrical structure, for instance on one side of the mid-sagittal plane. The tumour start region is preferably determined as the region where there is the highest concentration of enhanced voxels in the image. The tumour start region TSR is preferably selected so as to include at least some of the tumour.

The tumour start region TSR is preferably selected so as to include more enhanced voxels than non-enhanced voxels. In particular, the tumour start region can be determined on the basis of automatically detecting the tumour using automatic pathological detection and/or a longitudinal study. The tumour start region is in particular the most recently found region in which the tumour is present.

The tumour start region can for example be automatically determined as follows. A geometrical structure such as a sphere or a cube is grown in accordance with a predetermined procedure. For example, the radius of the sphere is successively increased by one voxel around a centre voxel. If the number of non-enhanced voxels grows more significantly than the number of enhanced voxels as the radius increases, then growing the geometric structure (sphere) is discontinued and the geometric structure (sphere) at the time of discontinuance is deemed to be a candidate tumour start region. This process is repeated for all the voxels. The candidate structure (sphere) which comprises the most enhanced voxels is then used as a start region. This is just one possible way of automatically determining the tumour start region.

Once the tumour start region has been acquired in accordance with step S50, a region-growing algorithm is then applied in step S60, starting with the voxels (image elements) in the tumour start region TSR. The voxels within the tumour start region TSR represent "seed points" for the region-growing algorithm. Preferably, each voxel in the start region represents a seed point for the region-growing algorithm. The enhanced voxels (i.e. those with an assigned value indicating an enhanced signal) within the tumour start region collectively define a structure which is referred to as the start structure, i.e. the set of enhanced voxels within the start region TSR represents the start structure. When the region-growing algorithm is applied, any enhanced voxel adjacent to the start structure is added to the start structure, hence the start structure "grows". All the enhanced voxels inside the start region (i.e. the start structure) have in particular been identified. This means in particular that only enhanced voxels outside the start region are added to the start structure in order to grow the start structure. A start structure which has grown due to the addition of enhanced voxels is referred to as a "growing structure", i.e. the region-growing algorithm adds enhanced voxels to the growing structure if the enhanced voxels are adjacent to the growing structure and in particular outside the start region. The region-growing algorithm is discontinued once there are no further enhanced voxels which are adjacent to the growing structure. Once the region-growing algorithm has been completed, the growing structure is then referred to as the final growing structure. The term "adjacent" as used herein is in particular understood to mean that a voxel is adjacent to a region, in particular to the growing structure, if the voxel is a neighbour of at least one other voxel of the region (in particular the growing structure). In two dimensions, for example, a neighbourhood can be a neighbourhood of four voxels (i.e. on the abutting sides of the voxel) or a neighbourhood of eight voxels (i.e. four voxels which exhibit abutting sides and four voxels which are connected via corners). Correspondingly, the neighbourhood of one voxel in three dimensions can consist of six voxels (the abutting surfaces) or twenty-six voxels (the abutting surfaces and the contacting corners and edges).

In the example shown in FIG. 4, the region-growing algorithm results in the growing structure "protruding" (in particular "leaking") beyond the tumour start region when the region growing algorithm is applied to the start structure.

The final growing structure which results from the application of the region-growing algorithm is shown as a hatched region in FIG. 4 and provided with the reference sign 220. The final growing structure 220 comprises substructures 221, 222, 223 and 224 which are linked by constrictions 225, 226 and 227. These substructures and constrictions are candidates for forming part of the tumour and are therefore referred to as candidate structures. Of the candidate structures, the substructure 221 is assumed to represent the structure of interest, such as for example the tumour, since a part 221' of the structure is located inside the start region TSR. This part 221' therefore constitutes the start structure. In accordance with one embodiment of the invention, the region-growing algorithm is modified (in particular supplemented by an additional step) in order to prevent candidate structures from protruding into non-habitat structures (see below) or beyond a habitat structure (see in particular the description pertaining to FIG. 5 below) or in order to reverse such a protrusion after it has been caused by the region growing algorithm.

The final growing structure can be modified by preventing the spread of the growing structure, in particular by restricting the application of the region-growing algorithm to parts of the binary image before or while the region-growing algorithm is applied and/or by changing the intensity of voxels in such a way that they do not fulfil the intensity condition before or while the region-growing algorithm is applied. Alternatively or additionally, the final growing structure can be modified after the region-growing application has been applied, by removing substructures from the final growing structure which are deemed to not represent a tumour, i.e. by reversing the protrusion ("leakage") manifested by these non-tumour substructures.

Embodiments in which the growing structure is modified before and/or after the region-growing algorithm is applied are discussed below.

In FIG. 5, the binary image BI" contains both a dotted structure 230 and a hatched structure 220'. The hatched structure 220' is smaller than the hatched structure 220 shown in FIG. 4. The structures 220' and 230 both consist of enhanced voxels. However, only the structure 220' has been identified as a structure of interest, i.e. a tumour. In particular, the candidate structures denoted in FIG. 4 as 222 and 224 and the candidate structure denoted in FIG. 5 as 223" (which in FIG. 4 is part of the substructure 223) have been determined as belonging to the structure 230, i.e. as not representing the structure of interest (tumour), such that only the substructures 221 and 223' (which is the other part of the substructure denoted as 223 in FIG. 4) and the constriction 226 are determined as being part of the hatched structure 220', i.e. as representing the structure of interest. The other substructures have been excluded by applying a brain mask to the binary image BI' of FIG. 4. The brain mask is designed to exclude all the candidate structures or parts of candidate structures which are part of the head but not the brain, such as for instance the eyes, skin, fat and bone. These parts can also be described as representing a "non-habitat structure", while the brain represents a "habitat structure" (with the exception of structures such as the vasculature). The terms "habitat structure" and "non-habitat structure" will be explained in more detail below. Applying the brain mask (in one particular procedure) therefore preferably removes a non-habitat structure from the binary image and/or extracts a structure from the binary image which at least primarily consists of a habitat structure. The brain mask is preferably applied before the region-growing algorithm. In this way, the growing structure can be prevented from protruding into particular sub-regions of the body part such as for example the region 237 in FIG. 5 (i.e. the brain). These particular sub-regions such as 237 are within the habitat structure and are linked to the start structure by the region-growing algorithm if the brain mask is not applied first. Once the brain mask has been applied, this link is eliminated, and these particular sub-regions can then be identified as not representing the structure of interest, since they are not linked to the start structure. Accordingly, they can then be removed from the final growing structure. The brain mask is preferably determined on the basis of the non-enhanced image but can also be determined on the basis of the enhanced image and/or the normalised difference image. The brain mask can be determined by so-called "skull stripping".

An anatomical atlas, in particular the so-called universal atlas (international patent application No. PCT/EP2012/071241 and international patent application No. PCT/EP2012/071239, both filed on 26 Oct. 2012), can be used to determine the brain mask by segmenting the parts of the head which contain brain tissue and combining the segmented parts to form the brain mask. Skull stripping procedures are described in Fennema-Notestine C. et al.: "Quantitative Evaluation of Automated Skull-Stripping Methods Applied to Contemporary and Legacy Images: Effects of Diagnosis, Bias Correction, and Slice Location" in Human Brain Mapping, Volume 27, Issue 2, February 2006, pages 99-113.

Alternatively, structures representing the brain and/or structures not representing the brain are segmented in one of the aforementioned images (the enhanced image, the non-enhanced image or the normalised difference image, but preferably the non-enhanced image) using an anatomical atlas. The segmentation process relies in particular on the geometrical properties and/or representational properties of the segmented structures. The atlas represents an example of property data which describe geometrical and/or representational properties of structures of the anatomical body part. In accordance with one embodiment, these properties are in particular used to extract a first type of structures in which the tumour is assumed or known to be embedded (and in which in particular the tumour can grow, such as for instance the brain tissue in the case of a brain tumour). The atlas can also describe the properties of a second type of structure in which the tumour is assumed to not reside and in particular in which it does not grow (such as fat, bone and dura mater in the case of a brain tumour). The set of structures of the first type is referred to here as the habitat structure, and the set of structures of the second type is referred to here as the non-habitat structure. In other words, the tumour is assumed or known to be present in a habitat structure but not in a non-habitat structure.

The geometrical properties and/or representational properties of structures can also be used to further process the normalised difference image before applying the intensity condition (threshold) to the normalised difference image.

In a following step S70, so-called greyscale reconstruction is used to remove intensity variations in the normalised difference image which could or would fulfil the intensity condition but which are nevertheless assumed to not represent a structure of interest due to their geometrical properties and in particular because they are located in a non-habitat structure. The intensity variations represent deviations from the background intensity. Applying greyscale reconstruction reduces and in particular eliminates this deviation. The structures which are represented by the intensity variations and are to be changed, in particular reduced to the background intensity, by greyscale reconstruction are in particular those which have geometrical properties which can be eliminated by applying a spatial filter to the normalised difference image. The spatial filter eliminates image features which have a high spatial frequency such as thin, lengthy structures (which for example represent vascular structures) which in particular have a ramification of branches. Preferably, lengthy structures having an average cross-section of less than 2 mm or less than 1 mm in their longitudinal extension are suppressed by applying greyscale reconstruction, in particular by applying the spatial filter.

With respect to greyscale reconstruction, reference is made in particular to Vincent, L.: "Morphological Grayscale Reconstruction in Image Analysis: Applications and Efficient Algorithms.", in IEEE Transactions on Image Processing, 2(2), 1993.

The left-hand side in FIG. 6A shows a tumour 100, a vascular structure 110 and a metastasis 120 before greyscale reconstruction is applied. The right-hand side in FIG. 6B shows the normalised difference image after greyscale reconstruction has been applied. As can be seen from a comparison of FIGS. 6A and 6B, the vascular structure 110 has been suppressed and only smaller, lower-intensity structures 110' remain, while the larger structures such as the tumour 100 and the metastasis 120 (which are not thin, lengthy structures) remain unchanged. Ideally, the remaining vascular structures 110' would have intensities which do not fulfil the intensity condition, such that the vascular structures 110' would be completely eliminated once the threshold has been applied, while the bulky structures of the tumour 100 and the metastasis 120 fulfil the intensity condition and are thus still visible in the binary image. The enhanced tumour is thus determined in accordance with these criteria in step S80.

Figure 7A:
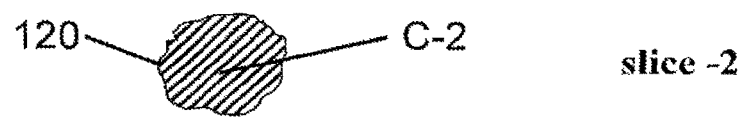
Figure 7B:
Figure 7C:
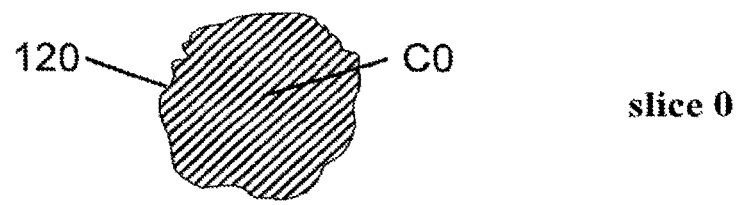
Figure 7D:
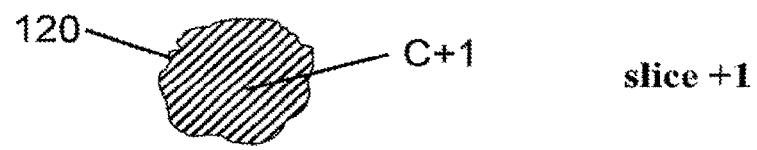
Figure 7E:
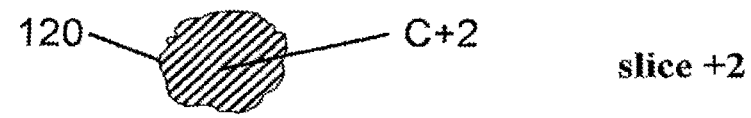

FIGS. 7A-E illustrate how a metastasis is detected. FIGS. 7A-C show the metastasis 120 as represented by different two-dimensional layers of voxel sets of the binary image. The voxel sets respectively comprise voxels which indicate an enhanced signal intensity and are integrally closed, i.e. not adjacent to other voxel sets and/or enhanced voxels. The layers are referred to as metastasis slices and are located one above the other. The slice −2 shown in FIG. 7A is the topmost slice. It is followed by a slice −1 which is shown in FIG. 7B. Below this slice, there is a slice 0 which is shown in FIG. 7C. This is followed by a slice +1 which is shown in FIG. 7D. Lastly, there is a slice +2 which is shown in FIG. 7E. As can be seen from FIGS. 7A-E as a whole, the size of the metastasis slices increases from slice −2 in FIG. 7A to slice 0 in FIG. 7C and then decreases from slice 0 in FIG. 7C to slice +2 in FIG. 7E. The slices are preferably analysed in order to check whether the metastasis is similar to a predefined (three-dimensional) geometry, in particular a sphere. In FIGS. 7A-E, the geometry of the metastasis 120 and the thickness of the slices are such that the metastasis has a shape which is similar to a sphere. The shape represented by the different slices is preferably analysed as to whether or not it is similar to a predetermined two-dimensional geometry (for example, a circle). In particular, the 2D geometry is analysed as to whether or not it is a two-dimensional manifestation of the predefined three-dimensional geometry. The 3D geometry and in particular the 2D geometry of the metastasis is described by metastasis geometry data. The relative sizes and positions of the circles in the different slices shown in FIGS. 7A to 7E are preferably also determined. A condition for such a positional relationship can for example be that the deviation in the centre of the circle from layer to layer is within a predetermined range of variation. The centre is indicated in each of FIGS. 7A to 7E by the reference sign C and the respective slice number, i.e. there is a centre at C−2, C−1, C0, C+1 and C+2. These are the centres of circles (not shown) which are preferably fitted to the boundary of the respective metastasis in FIGS. 7A to 7E. Preferably, the centres are located at least approximately one above the other. If, for example, all the centres are projected onto the plane of slice 0, then in accordance with a condition for the geometrical properties of the metastasis, all the centres are within a circle around the centre C0 which has a radius which is smaller than a predetermined percentage of the radius of the circle fitted to the metastasis 120 in slice 0. This percentage is preferably set to be lower than 20% or 10%.

Additionally, a condition can be set for fitting the circle to the boundary of the metastasis in the different layers. The standard deviation between the boundary and the circle can for example be determined so as to be less than a predetermined percentage of the radius of the fitted circle. This predetermined percentage is preferably lower than 20% or lower than 10%.

Aside from the above-mentioned conditions for the geometry of a metastasis, a condition for the size relationship can alternatively or preferably additionally be set. This condition can for example stipulate that the radius of the circle steadily decrease from a middle layer towards the outer layers, preferably in a manner which complies with the predetermined geometrical properties of a metastasis, i.e. which for example complies with a spherical shape of the metastasis.

FIG. 8 schematically shows a medical image processing system 300 comprising an analytical device 310 for generating a medical image of a patient 320 lying on a patient couch 330. The medical image processing system 300 also comprises a computer 340 which is connected to the analytical device 310, and a display device 342 which is connected to the computer 340. The aforementioned method is performed by means of a program which is loaded into the computer 340 and which can be run on the computer 340.

Definitions

The step of "determining an enhancing structure of interest" in particular means determining a representation of the enhancing structure of interest and in particular involves determining spatial information (which in particular includes the spatial position and/or geometry) concerning a part within a medical image, wherein said part is determined (in accordance with the present invention) to represent the enhancing structure of interest.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, in particular electrical, and in particular technically generated) signal wave, in particular a digital signal wave, carrying information which represents the program, in particular the aforementioned program, which in particular comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, in particular computer-readable data storage medium comprising computer-usable, in particular computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, in particular a data processing device comprising a digital processor (central processing unit or CPU) which executes the computer program elements, and optionally a volatile memory (in particular a random access memory or RAM) for storing data used for and/or produced by executing the computer program elements. Within the framework of the present invention, a computer-usable, in particular computer-readable data storage medium can be any data storage medium which can include, store, communicate, propagate or transport the program for use on or in connection with the instruction-executing system, apparatus or device. The computer-usable, in particular computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can in particular include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which in particular comprises technical, in particular tangible components, in particular mechanical and/or electronic components. Any device mentioned as such in this document is a technical and in particular tangible device.

Analytical devices such as x-ray devices, CT devices or MRT devices are used to generate analytical images (such as x-ray images or MRT images) of the body. Analytical devices use imaging methods, in particular so-called "medical imaging methods", for analysing a patient's body, for instance by using waves and/or radiation and/or energy beams, in particular electromagnetic waves and/or radiation, ultrasound waves and/or particles beams. Analytical devices are in particular devices which generate images (for example, two-dimensional or three-dimensional images) of the patient's body (and in particular of internal structures and/or anatomical parts of the patient's body) by analysing the body. The images are also referred to as "medical images". Analytical devices are in particular used in medical diagnosis, in particular in radiology.

In the field of medicine, imaging methods (also called medical imaging methods and/or imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based, in particular analytical device-based) imaging methods (so-called medical imaging modalities and/or radiological imaging methods) such as for instance computed tomography (CT) and cone beam computed tomography (CBCT, in particular volumetric CBCT), x-ray tomography, magnetic resonance tomography (MRT or MRI), conventional x-ray, sonography and/or ultrasound examinations, and positron emission tomography. Analytical devices in particular are used to generate the image data in apparatus-based imaging methods. The image data describe images which are also referred to as medical images. The imaging methods are in particular used for medical diagnostics, to analyse the anatomical body in order to generate images which are described by the image data. The imaging methods are also in particular used to detect pathological changes in the human body.

The method in accordance with the invention is in particular a data processing method. The data processing method is preferably performed using technical means, in particular a computer. The data processing method is preferably constituted to be executed by or on a computer and in particular is executed by or on the computer. In particular, all the steps or merely some of the steps (i.e. less than the total number of steps) of the method in accordance with the invention can be executed by a computer. The computer in particular comprises a processor and a memory in order to process the data, in particular electronically and/or optically. The calculating steps described are in particular performed by a computer. Determining steps or calculating steps are in particular steps of determining data within the framework of the technical data processing method, in particular within the framework of a program. A computer is in particular any kind of data processing device, in particular electronic data processing device. A computer can be a device which is generally thought of as such, for example desktop PCs, notebooks, netbooks, etc., but can also be any programmable apparatus, such as for example a mobile phone or an embedded processor. A computer can in particular comprise a system (network) of "sub-computers", wherein each sub-computer represents a computer in its own right. The term "computer" includes a cloud computer, in particular a cloud server. The term "cloud computer" includes a cloud computer system which in particular comprises a system of at least one cloud computer and in particular a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. In particular, the term "cloud" is used in this respect as a metaphor for the Internet (world wide web). In particular, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer in particular comprises interfaces in order to receive or output data and/or perform an analogue-to-digital conversion. The data are in particular data which represent physical properties and/or which are generated from technical signals. The technical signals are in particular generated by means of (technical) detection devices (such as for example devices for detecting marker devices) and/or (technical) analytical devices (such as for example devices for performing imaging methods), wherein the technical signals are in particular electrical or optical signals. The technical signals in particular represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer.

The expression "acquiring data" in particular encompasses (within the framework of a data processing method) the scenario in which the data are determined by the data processing method or program. Determining data in particular encompasses measuring physical quantities and transforming the measured values into data, in particular digital data, and/or computing the data by means of a computer and in particular within the framework of the method in accordance with the invention. The meaning of "acquiring data" also in particular encompasses the scenario in which the data are received or retrieved by the data processing method or program, for example from another program, a previous method step or a data storage medium, in particular for further processing by the data processing method or program. The expression "acquiring data" can therefore also for example mean waiting to receive data and/or receiving the data. The received data can for example be inputted via an interface. The expression "acquiring data" can also mean that the data processing method or program performs steps in order to (actively) receive or retrieve the data from a data source, for instance a data storage medium (such as for example a ROM, RAM, database, hard drive, etc.), or via the interface (for instance, from another computer or a network). The data can be made "ready for use" by performing an additional step before the acquiring step. In accordance with this additional step, the data are generated in order to be acquired. The data are in particular detected or captured (for example by an analytical device). Alternatively or additionally, the data are inputted in accordance with the additional step, for instance via interfaces. The data generated can in particular be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, in particular determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

Image fusion can be elastic image fusion or rigid image fusion. In the case of rigid image fusion, the relative position between the pixels of a 2D image and/or voxels of a 3D image is fixed, while in the case of elastic image fusion, the relative positions are allowed to change.

Elastic fusion transformations (for example, elastic image fusion transformations) are in particular designed to enable a seamless transition from one data set (for example a first data set such as for example a first image) to another data set (for example a second data set such as for example a second image). The transformation is in particular designed such that one of the first and second data sets (images) is deformed, in particular in such a way that corresponding structures (in particular, corresponding image elements) are arranged at the same position as in the other of the first and second images. The deformed (transformed) image which is transformed from one of the first and second images is in particular as similar as possible to the other of the first and second images. Preferably, (numerical) optimisation algorithms are applied in order to find the transformation which results in an optimum degree of similarity. The degree of similarity is preferably measured by way of a measure of similarity (also referred to in the following as a "similarity measure"). The parameters of the optimisation algorithm are in particular vectors of a deformation field. These vectors are determined by the optimisation algorithm in such a way as to result in an optimum degree of similarity. Thus, the optimum degree of similarity represents a condition, in particular a constraint, for the optimisation algorithm. The bases of the vectors lie in particular at voxel positions of one of the first and second images which is to be transformed, and the tips of the vectors lie at the corresponding voxel positions in the transformed image. A plurality of these vectors are preferably provided, for instance more than twenty or a hundred or a thousand or ten thousand, etc. Preferably, there are (other) constraints on the transformation (deformation), in particular in order to avoid pathological deformations (for instance, all the voxels being shifted to the same position by the transformation). These constraints include in particular the constraint that the transformation is regular, which in particular means that a Jacobian determinant calculated from a matrix of the deformation field (in particular, the vector field) is larger than zero, and also the constraint that the transformed (deformed) image is not self-intersecting and in particular that the transformed (deformed) image does not comprise faults and/or ruptures. The constraints include in particular the constraint that if a regular grid is transformed simultaneously with the image and in a corresponding manner, the grid is not allowed to interfold at any of its locations. The optimising problem is in particular solved iteratively, in particular by means of an optimisation algorithm which is in particular a first-order optimisation algorithm, in particular a gradient descent algorithm. Other examples of optimisation algorithms include optimisation algorithms which do not use derivations, such as the downhill simplex algorithm, or algorithms which use higher-order derivatives such as Newton-like algorithms. The optimisation algorithm preferably performs a local optimisation. If there is a plurality of local optima, global algorithms such as simulated annealing or generic algorithms can be used. In the case of linear optimisation problems, the simplex method can for instance be used.

In the steps of the optimisation algorithms, the voxels are in particular shifted by a magnitude in a direction such that the degree of similarity is increased. This magnitude is preferably less than a predefined limit, for instance less than ⅒ or 1/100 or 1/1000 of the diameter of the image, and in particular about equal to or less than the distance between neighbouring voxels. Large deformations can be implemented, in particular due to a high number of (iteration) steps.

The determined elastic fusion transformation can in particular be used to determine a degree of similarity (or similarity measure, see above) between the first and second data sets (first and second images). To this end, the deviation between the elastic fusion transformation and an identity transformation is determined. The degree of deviation can for instance be calculated by determining the difference between the determinant of the elastic fusion transformation and the identity transformation. The higher the deviation, the lower the similarity, hence the degree of deviation can be used to determine a measure of similarity.

A measure of similarity can in particular be determined on the basis of a determined correlation between the first and second data sets. It is possible to decide whether or not there is similarity by means of such a similarity measure (see Definitions) and in particular by means of a predetermined (percentage) threshold. The term "similar" as used here encompasses the term "identical". Similarity may for example be assumed if the deviation from identity is less than 30%, in particular less than 20% and preferably less than 10%.

The method in accordance with the invention is preferably at least partly executed by a computer, i.e. all the steps or merely some of the steps (i.e. less than the total number of steps) of the method in accordance with the invention can be executed by a computer.

The invention claimed is:

1. A medical system for determining metastases in an image of an anatomical body part, comprising:
   an analytical device for generating images of an anatomical body part;
   at least one computer operable to receive the images from the analytical device and having at least one processor and memory with instructions, the analytical device operable to receive an enhanced image of the anatomical body part using a contrasting agent and receive a non-enhanced image of the anatomical body part without using the contrasting agent, the instructions, when executed on the computer, configuring the computer to:
   spatially correlate the enhanced image and the non-enhanced image to create a common reference system;
   wherein both the enhanced image and the non-enhanced image include two dimensional layers of voxels;
   transform at least one of the enhanced image and the non-enhanced image to create a bijective assignment between the voxels and the respective image;
   create a normalized difference image and acquire a non-tumor region in both the enhanced image and the non-enhanced image;
   wherein each of the voxels of the enhanced image and the voxels of the non-enhanced image have voxel intensities and wherein the normalized difference image has a plurality of voxels each with an associated voxel intensity;
   acquire an intensity threshold of the normalized difference image to differentiate between the voxel intensities caused by the contrast agent and the voxel intensities not caused by the contrast agent;
   using the intensity threshold to determine a three-dimensional binary image,
   acquire metastasis geometry data which describe geometrical properties of a metastasis in the binary image;
   determine a set of adjacent image elements;
   analyze the 2D properties of the set; and
   determine that the set represents a metastasis if the set exhibits two-dimensional geometrical properties which comply with the geometrical properties described by the metastasis geometry data.

2. The system of claim 1 the wherein both the enhanced image and the non-enhanced image include the two dimensional layers of voxels positioned one above the other.

3. The system of claim 1 wherein the bijective assignment between the voxels and the respective image are created so that a 1:1 correspondence between the voxels in the respective image is established.

4. The system of claim 1 wherein the binary image comprises a plurality of image layers which comprise a plurality of pixels.

5. The system of claim 4 wherein the binary image is a three-dimensional image and comprises a plurality of image layers which comprise a plurality of pixels.

6. The system of claim 1 the set of adjacent image elements represent the enhanced signal intensity and are integrally closed and apart from other sets and/or image elements which represent the enhanced signal intensity.

7. A computer implemented method for determining metastases within an anatomical body part, wherein the metastases exhibits an enhanced signal in an image of the anatomical body part generated by a medical imaging method using a contrast agent, the method being designed to be performed by a computer and comprising the following steps:
   acquiring an enhanced image of the anatomical body part obtained by a medical imaging method using the contrast agent;
   acquiring a non-enhanced image of the anatomical body part obtained by a medical imaging method without using the contrast agent;
   spatially correlating the enhanced image and the non-enhanced image with respect to each other;
   acquiring non-enhanced sub-regions in each of the enhanced image and the non-enhanced image, wherein the non-enhanced sub-regions are assumed or known to not exhibit an enhanced signal;
   determining a normalized difference image by normalizing the spatially correlated enhanced and non-enhanced images with respect to each other on the basis of the intensities in the respective non-enhanced sub-regions and by performing a difference operation on the normalized spatially correlated enhanced and non-enhanced images;
   acquiring an intensity condition for differentiating between the structure of interest and other structures which do not exhibit an enhanced signal;
   determining a binary image on the basis of the intensity condition and the normalized difference image, wherein the binary image comprises image elements representing either an enhanced signal intensity or a non-enhanced signal intensity;
wherein the binary image is a three-dimensional image and comprises a plurality of image layers which comprise a plurality of pixels and the method further comprising the steps of:

acquiring metastasis geometry data which describe geometrical properties of a metastasis in the image layers;
determining a set of adjacent image elements which represent the enhanced signal intensity and are integrally closed and apart from other sets and/or image elements which represent the enhanced signal intensity;
analyzing the 2D properties of the set; and
determining that the set represents a metastasis if the set exhibits two-dimensional geometrical properties which comply with the geometrical properties described by the metastasis geometry data.

8. The method according to claim 7, wherein the geometrical properties include relative geometrical properties, which describe the relative variation in the geometry of the metastasis of one image layer with respect to another image layer.

9. The method according to claim 8, wherein the another image layer is an adjacent image layer.

10. The method according to claim 7, wherein the set is determined to represent a metastasis if the analyzed 2D properties of the set exhibit two-dimensional geometrical properties which match the geometrical properties described by the metastasis geometry data.

11. The method according to claim 10, wherein the geometrical property is that the borderline of the set has a shape similar to a circle.

12. The method according to claim 11, wherein the set is identified to represent a metastasis if combined slices of the set are similar to a spherical shape.

13. The method according to claim 7 wherein the set is identified to represent a metastasis if slices of the set are arranged concentrically.

14. The method according to claim 7, wherein a two-dimensional layer of image elements from the set is referred to as a metastasis slice, and wherein the metastasis geometry data describe a metastasis as exhibiting at least one of the following features:
 the metastasis slices are in adjacent image layers;
 a shape of the metastasis slices arranged one above the other in adjacent image layers is similar;
 the size of a metastasis slice between two other metastasis slices is larger than the size of at least one of the two other metastasis slices.

15. A method of enhancing a structure of interest within an anatomical body part in an image of the body part, comprising:

acquiring an enhanced image of the anatomical body part obtained by medical imaging using a contrasting agent;
acquiring a non-enhanced image of the anatomical body part obtained by medical imaging without using the contrasting agent;
spatially correlating the enhanced image and the non-enhanced image to create a common reference system;
wherein both the enhanced image and the non-enhanced image include two dimensional layers of voxels positioned one above the other;
transforming at least one of the enhanced image and the non-enhanced image to create a bijective assignment between the voxels and the respective image so that a 1:1 correspondence between the voxels in the respective image is established;
creating a normalized difference image and acquiring a non-tumor region in both the enhanced image and the non-enhanced image;
wherein each of the voxels of the enhanced image and the voxels of the non-enhanced image have voxel intensities and wherein the normalized difference image has a plurality of voxels each with an associated voxel intensity;
acquiring an intensity threshold of the normalized difference image to differentiate between the voxel intensities caused by the contrast agent and the voxel intensities not caused by the contrast agent,
wherein the binary image is a three-dimensional image and comprises a plurality of image layers which comprise a plurality of pixels and the method further comprising the steps of:
acquiring metastasis geometry data which describe geometrical properties of a metastasis in the image layers;
determining a set of adjacent image elements which represent the enhanced signal intensity and are integrally closed and apart from other sets and/or image elements which represent the enhanced signal intensity;
analyzing the 2D properties of the set; and
determining that the set represents a metastasis if the set exhibits two-dimensional geometrical properties which comply with the geometrical properties described by the metastasis geometry data.

* * * * *

UNITED STATES PATENT AND TRADEMARK OFFICE
CERTIFICATE OF CORRECTION

PATENT NO. : 10,056,158 B2  
APPLICATION NO. : 15/819995  
DATED : August 21, 2018  
INVENTOR(S) : Rainer Lachner, Rowena Thomson and Christina von Freyberg Page 1 of 1

It is certified that error appears in the above-identified patent and that said Letters Patent is hereby corrected as shown below:

On the Title Page

Item (57) Abstract: "wherein the structure of interest" should be "wherein a structure of interest"

In the Claims

Claim 2, Column 28, Line 13: "claim 1 the wherein" should be "claim 1, wherein"

Claim 3, Column 28, Line 14: "claim 1 wherein" should be "claim 1, wherein"

Claim 4, Column 28, Line 20: "claim 1 wherein" should be "claim 1, wherein"

Claim 5, Column 28, Line 23: "claim 4 wherein" should be "claim 4, wherein"

Claim 6, Column 28, Line 26: "claim 1 the set" should be "claim 1, wherein the set"

Signed and Sealed this  
Ninth Day of April, 2019

Andrei Iancu  
*Director of the United States Patent and Trademark Office*